United States Patent
Dinca et al.

(10) Patent No.: US 7,505,562 B2
(45) Date of Patent: Mar. 17, 2009

(54) X-RAY IMAGING OF BAGGAGE AND PERSONNEL USING ARRAYS OF DISCRETE SOURCES AND MULTIPLE COLLIMATED BEAMS

(75) Inventors: Dan-Cristian Dinca, Billerica, MA (US); Richard Mastronardi, Medfield, MA (US); Peter J. Rothschild, Boston, MA (US)

(73) Assignee: American Science and Engineering, Inc., Billerica, MA (US)

( * ) Notice: Subject to any disclaimer, the term of this patent is extended or adjusted under 35 U.S.C. 154(b) by 10 days.

(21) Appl. No.: 11/737,317

(22) Filed: Apr. 19, 2007

(65) Prior Publication Data

US 2007/0258562 A1 Nov. 8, 2007

Related U.S. Application Data

(60) Provisional application No. 60/794,295, filed on Apr. 21, 2006.

(51) Int. Cl.
*G01N 23/201* (2006.01)
(52) U.S. Cl. .......................................... 378/87; 378/57
(58) Field of Classification Search .................. 378/37, 378/57, 86–90
See application file for complete search history.

(56) References Cited

U.S. PATENT DOCUMENTS

| | | | |
|---|---|---|---|
| 3,961,186 A | 6/1976 | Leunbach | 250/272 |
| 4,064,440 A | 12/1977 | Roder | 250/359 |
| 4,380,817 A | 4/1983 | Harding et al. | 378/87 |
| 4,525,854 A | 6/1985 | Molbert et al. | 378/89 |
| 4,799,247 A | 1/1989 | Annis et al. | 378/87 |
| 4,809,312 A | 2/1989 | Annis | 378/146 |
| 4,825,454 A | 4/1989 | Annis et al. | 378/87 |
| 4,864,142 A | 9/1989 | Gomberg | 378/57 |
| 4,870,670 A | 9/1989 | Geus | 378/87 |
| 5,179,581 A | 1/1993 | Annis | 378/57 |
| 5,247,561 A | 9/1993 | Kotowski | 378/87 |
| 5,394,454 A | 2/1995 | Harding | 378/86 |
| 5,430,787 A | 7/1995 | Norton | 378/87 |

(Continued)

FOREIGN PATENT DOCUMENTS

EP   0 261 984   3/1988

(Continued)

OTHER PUBLICATIONS

Zhang et al., A Multi-beam X-ray Imaging System Based on Carbon Nanotube Field Emitters, Medical Imaging 2006, Proceedings of SPIE, vol. 6142, Mar. 2, 2006.

(Continued)

*Primary Examiner*—Hoon Song
(74) *Attorney, Agent, or Firm*—Bromberg & Sunstein LLP

(57) ABSTRACT

A system and methods are provided for imaging an object, based on activating an array of discrete X-ray sources in a prescribed temporal pattern so as to illuminate the object with a beam varying in spatial orientation, and detecting X-rays of the beam after interaction with the object and generating a detector signal. An image of the object may then be constructed on the basis of the time variation of the detector signal. The discrete X-ray sources may be moved during the course of inspection, moreover, the prescribed temporal pattern may constitute a Hadamard code. The discrete sources may be carbon nanotube x-ray sources.

13 Claims, 7 Drawing Sheets

U.S. PATENT DOCUMENTS

| | | | | |
|---|---|---|---|---|
| 5,638,420 | A | 6/1997 | Armistead | 378/57 |
| 5,692,028 | A | 11/1997 | Geus et al. | 378/57 |
| 5,692,029 | A | 11/1997 | Husseiny et al. | 378/88 |
| 5,696,806 | A | 12/1997 | Grodzins et al. | 378/86 |
| 5,763,886 | A | 6/1998 | Schulte | 250/358.1 |
| 5,764,683 | A | 6/1998 | Swift et al. | 378/57 |
| 5,910,973 | A | 6/1999 | Grodzins | 378/57 |
| 5,974,111 | A | 10/1999 | Krug et al. | 378/57 |
| 6,018,562 | A | 1/2000 | Willson | 378/9 |
| 6,081,580 | A | 6/2000 | Grodzins et al. | 378/87 |
| 6,094,472 | A | 7/2000 | Smith | 378/86 |
| 6,151,381 | A | 11/2000 | Grodzins et al. | 378/90 |
| 6,192,104 | B1 | 2/2001 | Adams et al. | 378/90 |
| 6,212,251 | B1 | 4/2001 | Tomura et al. | 378/15 |
| 6,236,709 | B1 | 5/2001 | Perry et al. | 378/57 |
| 6,249,567 | B1 | 6/2001 | Rothschild et al. | 378/88 |
| 6,421,420 | B1 | 7/2002 | Grodzins | 378/98.6 |
| 6,442,233 | B1 | 8/2002 | Grodzins et al. | 378/57 |
| 6,459,761 | B1 | 10/2002 | Grodzins et al. | 378/57 |
| 6,473,487 | B1 | 10/2002 | Le | 378/57 |
| 6,553,096 | B1 * | 4/2003 | Zhou et al. | 378/122 |
| 6,567,496 | B1 | 5/2003 | Sychev | 378/57 |
| 6,876,719 | B2 | 4/2005 | Ozaki | 378/7 |
| 6,879,657 | B2 | 4/2005 | Hoffman | 378/7 |
| 2002/0122533 | A1 * | 9/2002 | Marie et al. | 378/196 |
| 2005/0190878 | A1 | 9/2005 | De Man et al. | 378/9 |
| 2005/0226371 | A1 * | 10/2005 | Kautzer et al. | 378/37 |
| 2007/0009088 | A1 | 1/2007 | Edic et al. | 378/62 |

FOREIGN PATENT DOCUMENTS

| | | |
|---|---|---|
| EP | 0 864 884 | 7/2006 |
| GB | 2 277 013 | 10/1994 |
| WO | 98/02763 | 1/1998 |
| WO | 98/03889 | 1/1998 |
| WO | 98/20366 | 5/1998 |

OTHER PUBLICATIONS

Cheng et al., Dynamic radiography using a carbon-nanotube-based field-emission x-ray source, Review of Scientific Instruments, vol. 75, No. 10, Oct. 2004.

Zhang et al., Stationary scanning x-ray source based on carbon nanotube field emitters, Applied Physics Letters 86, 184104, 2005.

Gindi et al., Imaging with rotating slit apertures and rotating collimators, Med. Phys. vol. 9, No. 3, May/Jun. 1982.

Zhang et al., A nanotube-based field emission x-ray source for microcomputed tomography, Review of Scientific Instruments 76, 094301, 2005.

Mertz et al., Rotational aperture synthesis for x rays, J. Opt. Soc. Am. A., vol. 3, No. 12, pp. 2167-2170, Dec. 1986.

Chou, Fourier coded-aperture imaging in nuclear medicine, IEE Proc.-Sci. Meas. Technol., vol. 141, No. 3, pp. 179-184, May 1994.

*International Search Report*, International Application No. PCT/US98/18642; Date of Mailing: Jul. 7, 1999.

*International Preliminary Examination Report*, International Application No. PCT/US98/18642; Date of Mailing: Aug. 30, 1999.

*International Search Report*, International Application No. PCT/US99/28266; Date of Mailing: Jun. 6, 2000.

*International Search Report*, International Application No. PCT/US99/28035; Date of Mailing: Sep. 15, 2000.

*Written Opinion*, International Application No. PCT/US99/28035; Date of Mailing: Apr. 20, 2001.

*International Preliminary Examination Report*, International Application No. PCT/US99/28035; Date of Completion of this Report: Mar. 25, 2002.

*International Search Report and Written Opinion of the International Searching Authority*, International Application No. PCT/US2005/011382; Date of Mailing: Oct. 21, 2005.

*International Preliminary Report on Patentability*, International Application No. PCT/US2005/011382; Date of Mailing: Oct. 19, 2006.

*Written Opinion of the International Searching Authority*, International Application No. PCT/US2007/066936; Date of Mailing: Sep. 30, 2008.

*International Search Report*, International Application No. PCT/US2007/066936; Date of Mailing: Sep. 30, 2008.

* cited by examiner

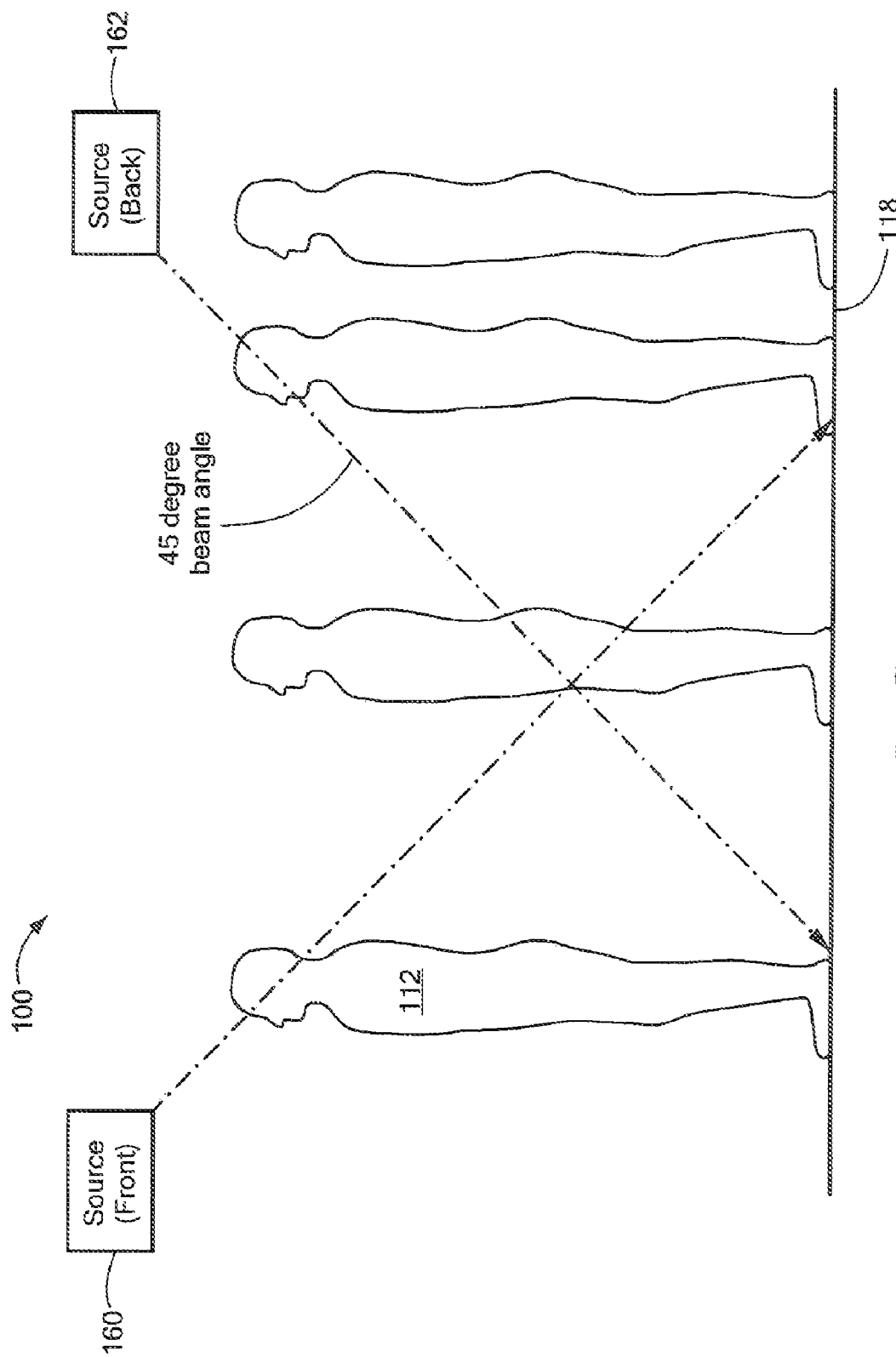

X-RAY IMAGING OF BAGGAGE AND PERSONNEL USING ARRAYS OF DISCRETE SOURCES AND MULTIPLE COLLIMATED BEAMS

The present application claims priority on the basis of U.S. Provisional Patent Application Ser. No. 60/794,295, entitled "X-ray Imaging using Arrays of Discrete to Sources," filed on Apr. 21, 2006, incorporated herein by reference.

TECHNICAL FIELD

The present invention relates to methods and systems for inspecting objects, including personnel but not limited thereto, by means of penetrating radiation, and more particularly, to inspection of personnel using multiple x-ray sources that may be individually activated.

BACKGROUND OF THE INVENTION

Conventional X-ray sources typically use a thermionic emission mechanism to produce electrons that impinge on a metallic target from which x-rays are emitted through bremsstrahlung processes. Thermionic emission entails the emission of electrons by heated filaments. Thermal inertia limits the time resolution of thermionic systems to microseconds, while spatial resolution of the electron emitter is governed by the dimension of the filament.

X-ray sources may also be based on field-emission cathodes, offering advantages in both spatial and temporal resolution when compared with thermionic sources. Because field emission of electrons is produced by a high electric field, no heating is necessary, whence such electron emitters are commonly referred to as cold cathodes. The electron beams emitted by such devices may have low divergence and thus provide ease of focusing. Moreover, the virtually instantaneous response of the source offers time gating capabilities comparable with the time resolution of the control circuit, and may be as fast as nanoseconds, using current technology.

Zhang et al., *A Multi-beam X-ray Imaging System Based on Carbon Nanotube Field Emitters*, in *Medical Imaging* 2006, (Proceedings of SPIE, Vol. 6142, Mar. 2, 2006), reported the fabrication, by Xintek, Inc. of Research Triangle Park, N.C., of a linear array of 5 X-ray sources, each with a focal spot between 200 and 300 μm, based on the use of carbon nanotube (CNT) electrodes. Electron currents in the range of 0.1-1 mA were reported at an accelerating voltage of 40-60 kVp. The lifetime of the cold cathode was estimated to exceed 2000 hours. For an accelerating voltage of 200 kV, a beam current of 13 mA has been measured. The aforesaid Zhang et al. paper is incorporated herein by reference. Devices with 1000 pixels per meter and pulse repetition rates on 10 MHz can be envisioned with technology within the current state of the art.

The use of CNT cold cathodes in the context of an X-ray source is also described by Cheng et al., *Dynamic radiography using a carbon-nanotube-based field-emission X-ray source*, 75 *Rev. Sci. Instruments*, p. 3264 (2004), while the use of CNT cold cathode source arrays in a scanning context is described by Zhang et al., *Stationary scanning x-ray source based on carbon nanotube field emitters*, 86 Appl. Phys. Lett., p. 184104 (2005), both of which articles are incorporated herein by reference.

Moreover, the use of CNT cold cathode source arrays in tomography is discussed by Zhang et al., *A nanotube-based field emission x-ray source for microcomputed tomography*, 76 *Rev. Sci. Instruments*, p. 94301 (2005), which is also incorporated herein by reference.

The footprint and throughput of personnel inspection equipment at airports have become increasingly important considerations as security checkpoints become more congested. Typically the critical dimension is that which is perpendicular to the flow of traffic, and currently deployed metal detectors are used as a standard of comparison. At US airports, the desired throughput is consistent with support of two adjacent baggage systems. This translates to a throughput of approximately 400 people per hour.

While backscatter x-ray scanning of personnel is often considered the most effective method for detection of concealed contraband goods or potential threats, current implementations of this technology may provide inadequate throughput for certain applications, and, moreover, may fail to meet size constraints imposed by certain venues such as airports. The present invention advantageously provides a solution to these shortcomings.

Current solutions that attempt to improve throughput over single-sided backscatter screening rely on several single point focus x-ray sources. Because the x-ray beam of these sources is collimated into a fan beam shaped line of x-rays, the angle of incidence on the person being screened can cause distortion in the image data. Even though the distortion can be compensated for in software, the data still derive from x-rays that vary in incident angle. At steep angles this can result in x-ray incident shadows (from body parts such as shoulders) and thus, in turn, cause concealed contraband to be missed. If several conventional x-ray sources are used to mitigate this effect, the equipment size becomes large and the equipment cost becomes unattractive.

SUMMARY OF THE INVENTION

In accordance with preferred embodiments of the present invention, a method is provided for imaging an object. The method entails:

a. activating an array of discrete X-ray sources in a prescribed temporal pattern so as to illuminate the object with a beam varying in spatial orientation;

b. detecting X-rays of the beam after interaction with the object and generating a detector signal; and c. constructing an image of the object based on the time variation of the detector signal.

Other embodiments of the invention may also include moving the array of discrete X-ray sources, either by rotation or by translation, or both. Characterizing the array of discrete X-ray sources by an array axis, the step of translating the array may include translating the array in a direction substantially transverse to the array axis, or rotating the array, about an axis substantially parallel to the array axis.

The prescribed temporal pattern of the invention, in certain embodiments, may constitute a Hadamard code. Moreover, the step of detecting X-rays after interaction with the object may include detecting N-rays scattered by the object, and the step of activating discrete X-ray sources may include activating field emission sources, and, more particularly, activating a plurality of field emission sources, each field emission source including a reflective target or a transmission target.

In accordance with further embodiments of the invention, an inspection system is provided for inspecting an object. The inspection system has a plurality of linear arrays of discrete sources of penetrating radiation, at least one scatter detector configured to generate a scatter signal based upon detection of penetrating radiation scattered by the inspected object, and a processor for receiving the scatter signal and generating an image of the object. The discrete sources of penetrating radiation, more particularly, may be carbon nanotube x-ray sources.

BRIEF DESCRIPTION OF THE DRAWINGS

The foregoing features of the invention will be more readily understood by reference to the following detailed description taken with the accompanying drawings:

FIG. 6B shows a schematic side view of an embodiment of the present invention, depicting a person at successive positions traversing a plurality of x-ray beams emitted from above;

DETAILED DESCRIPTION OF PREFERRED EMBODIMENTS

Figure 1:
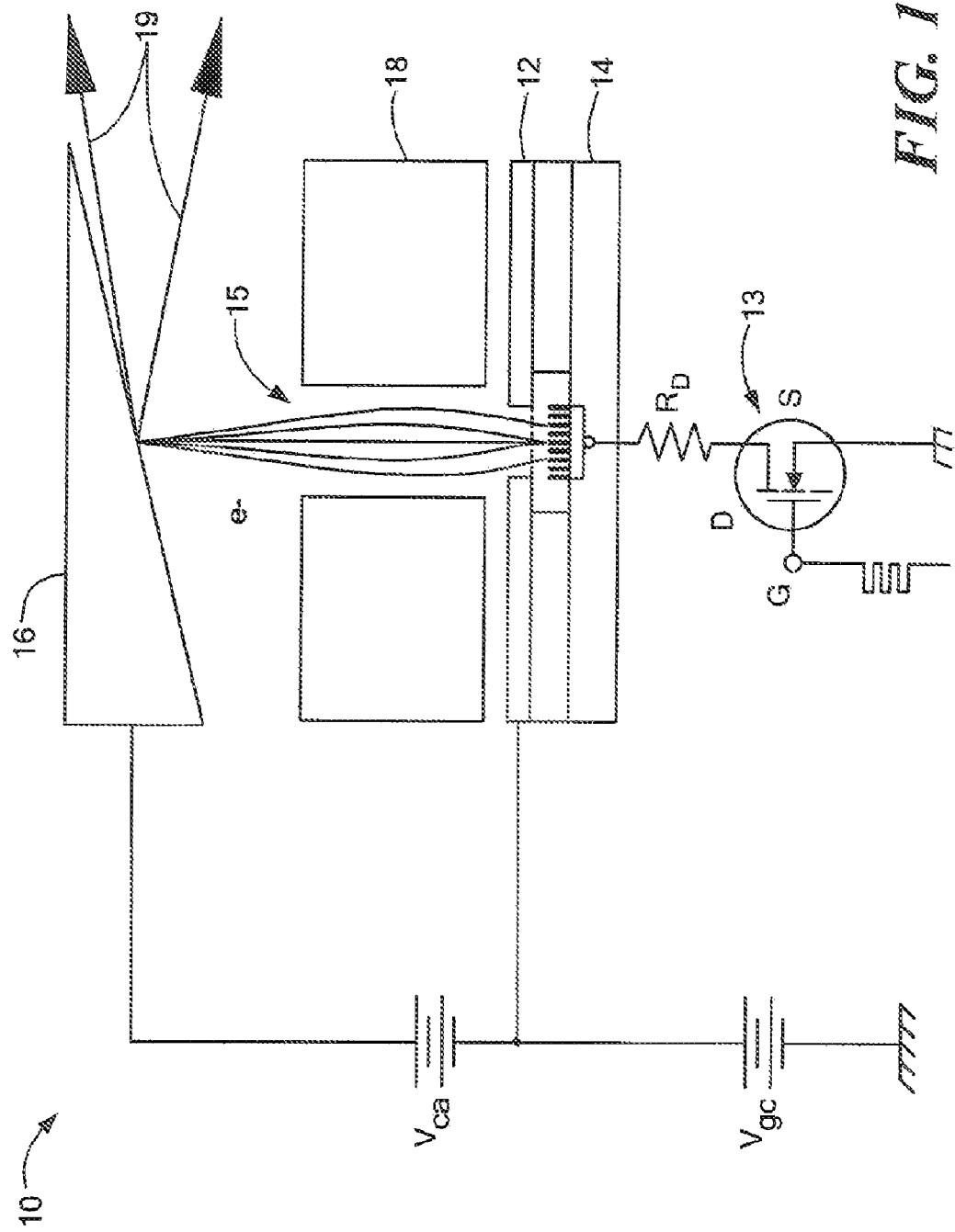
FIG. 1 is a schematic depiction of a prior art X-ray source based on electron field emission.

Cold cathode technology, such as that based on carbon nanotubes (CNTs), opens up the possibility of new modalities for imaging using X-rays, whether by transmission, backscatter, or forward scatter of the X-rays. Applied in the manner described below in accordance, with the present invention, discrete cold cathode sources may advantageously provide for electronically turning on the sources, and with low latency (on the nanosecond scale), in a sequential manner, thereby forming pencil beams, as often practiced in the X-ray imaging arts, or, alternatively, selecting a pattern of sources at a given time to form coded beams. The development of CNTs has allowed important technical challenges related to current stability and cathode life time to be overcome.

The general operation of a cold cathode X-ray source, designated generally, in FIG. 1, by numeral 10, is well understood in the art and is described with reference to FIG. 1. The cold cathode arrangement advantageously allows for a high degree of control. Voltage $V_{gc}$ between gate 12 and cathode 14, governed by control circuit 13, controls the current of electrons 15, while voltage $V_{ca}$ between cathode 14 and anode 16, which also serves as the X-ray target, controls the electron energy impinging on the target 16, and the voltage applied on the focusing electrode 18 determines the electron beam spot size.

While FIG. 1 depicts an assembly in which the X-rays are generated via a reflection target 19, a transmission target may also be employed within the scope of the present invention.

Application of discrete X-ray sources for X-ray imaging, in accordance with the present invention, varies with the dimensionality of the X-ray source array (one-, two-, or three-dimensional), the scanning mode (raster or pattern), the dynamic use of different or varying energies, and the use of time gating.

The time resolution capabilities can be of particularly advantage in long-range applications in which air scatter strongly affects the signal to noise ratio (SNR).

A first embodiment of the invention is described with reference to FIG. 2. A one-dimensional array 20 of X-ray sources 22 is disposed with backscatter detectors 23 on one or more sides of its longitudinal (typically vertical) axis 21. The entire device 24 can translate in a transverse direction 25, typically horizontally, so as to create an image on a line-by-line basis. Alternatively, array 20 may rotate about longitudinal (typically vertical) axis 21 such that X-ray beam 26 sweeps in a transverse direction (again, typically horizontally), thereby creating a line-by-line image, but without the entire device moving. Such system is suitable for a bomb-detection application, for example, wherein an X-ray image must be created in short time and without moving the entire imaging system, which may be disposed, for example, within a van. An image line is created by raster scanning the sources vertically by turning on one source 22 at a time in rapid succession.

In accordance with another embodiment of the present invention, coded beams are employed, based on Hadamard- or otherwise coded beams. A discussion of beam coding is to be found, for example, in Chou, *Fourier coded-aperture imaging in nuclear medicine*, in *IEE Proc. Sci. Meas. Technol.*, vol. 141, pp. 179-84 (1994), Mertz et al., *Rotational aperture synthesis for x rays*, in *J. Opt. Soc. Am. A*, vol. 3, pp. 2167-70 (1986), and in Gindi et al. *Imaging with rotating slit apertures and rotating collimators*, in *Med. Phys.*, vol. 9, pp. 324-39 (1982), all of which are incorporated herein by reference.

Field emission X-ray sources may be readily switched on and off electronically at significant rates, typically as rapidly as 30 kHz. This means that coded beams can be switched (changed from one pattern to another), cycled (the equivalent of rotation), or negated (switched from mask to antimask to reduce artifacts for close range imaging). The Hadamard-coded or patterned beams may be used to particular advantage when the X-ray flux is an issue.

Figure 3:
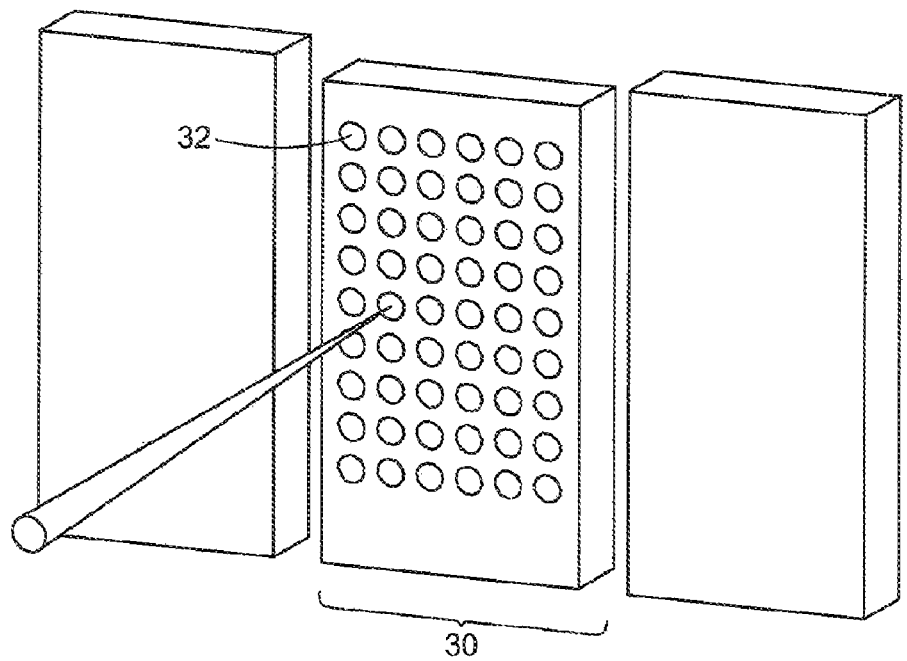
FIG. 3 shows the use of a two-dimensional array of discrete sources in a backscatter imaging application, in accordance with a preferred embodiment of the present invention.

Referring now to FIG. 3, a two-dimensional source array 30 may have no mechanically moving pants and allow coverage of a predefined solid angle (determined by the total number of sources 32 and their divergence) in a very short time. It can use a raster scan mechanism similar to a CRT or pattern beams (Hadamard or other coding mechanism).

In accordance with further embodiments of the present invention, a system with controlled velocity, designated generally by numeral 40, is described with reference to FIG. 4. One or more backscatter detectors 42 are fixed, but the source array 44 is translated with a constant speed back and forth in direction 45 adjacent to, or between, detectors 42. Such system may also be employed in an interlaced mode, described below. Embodiment of FIG. 4 may be employed to overcome a disadvantage of the embodiment of FIG. 2 namely a propensity to image distortions due to variations in the system velocity. Depending on the velocity of array 20, the objects may appear compressed or elongated.

Figure 5:
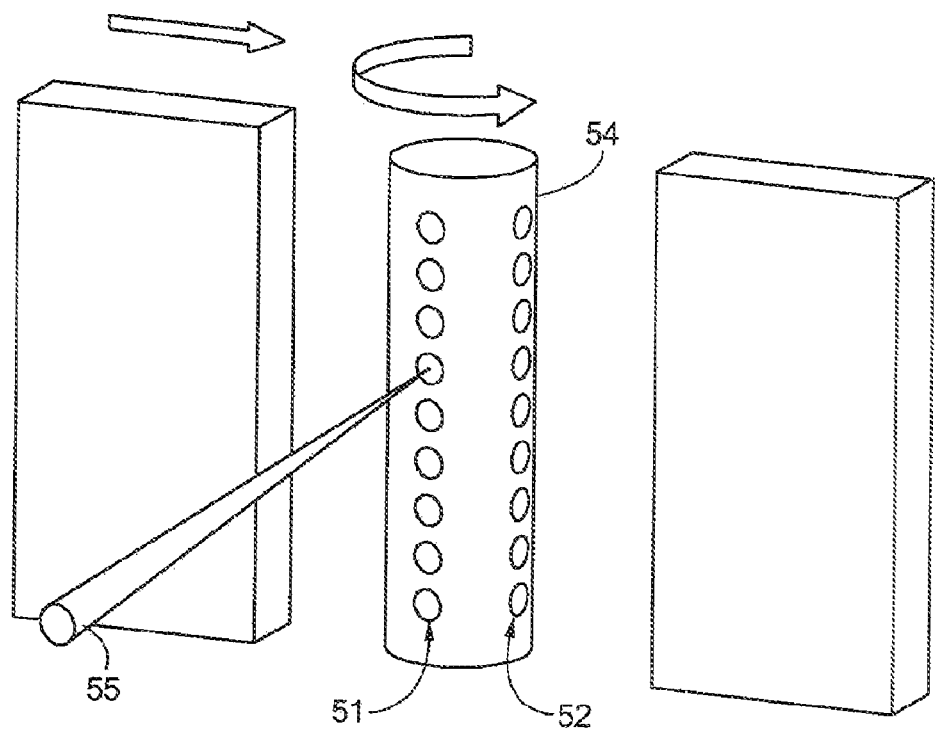
FIG. 5 shows an image generation apparatus in which multiple one-dimensional source arrays are mounted on a single cylinder, in accordance with an embodiment of the present invention.

Further versatility may be achieved using an embodiment such as that shown in FIG. 5 where two or more one-dimensional X-ray source arrays 51, 52, are mounted on a cylinder 54. Because the arrays can be turned on and off electronically with high speed, only the array generating an X-ray beam 55 that is illuminating a target (not shown) is turned on, and the other arrays are off, hence there is no need to shield one array from another. The versatility of this model resides in its natural ability to incorporate the interlaced mode, as now described, and to continuously accumulate an image.

Interlacing can be useful in cases where, due to technical limitations or by design, the minimum distance between two sources is 1 cm, but the required resolution for a specific applications demands sources placed 4 mm apart. On a cylinder, three one-dimensional arrays are placed at 120 degrees one from another and shifted vertically by 3.33 mm. Each array will scan lines 1 cm apart, but because of the vertical shift, the resulting image for a complete rotation of the cylinder will have a resolution of 3.33 mm. This mode of operation is referred to as "interlaced mode." For the system depicted in FIG. 4, interlaced imaging may be provided via vertical translation of the array for each horizontal pass.

Figure 2:
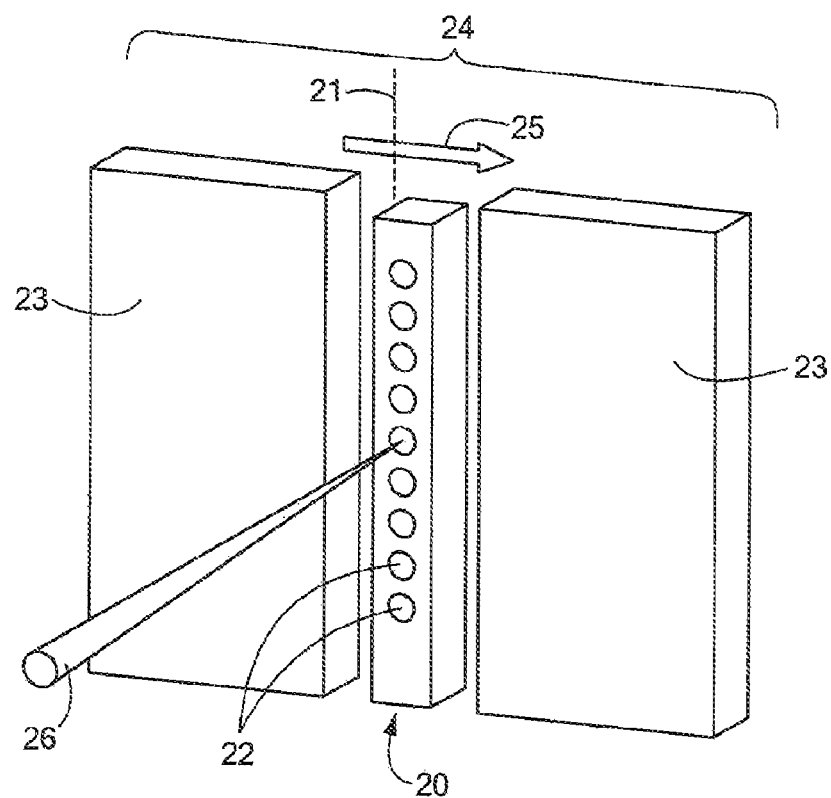
FIG. 2 shows the use of a single-dimensional array of discrete sources in a backscatter imaging application, in accordance with a preferred embodiment of the present invention.
Figure 4:
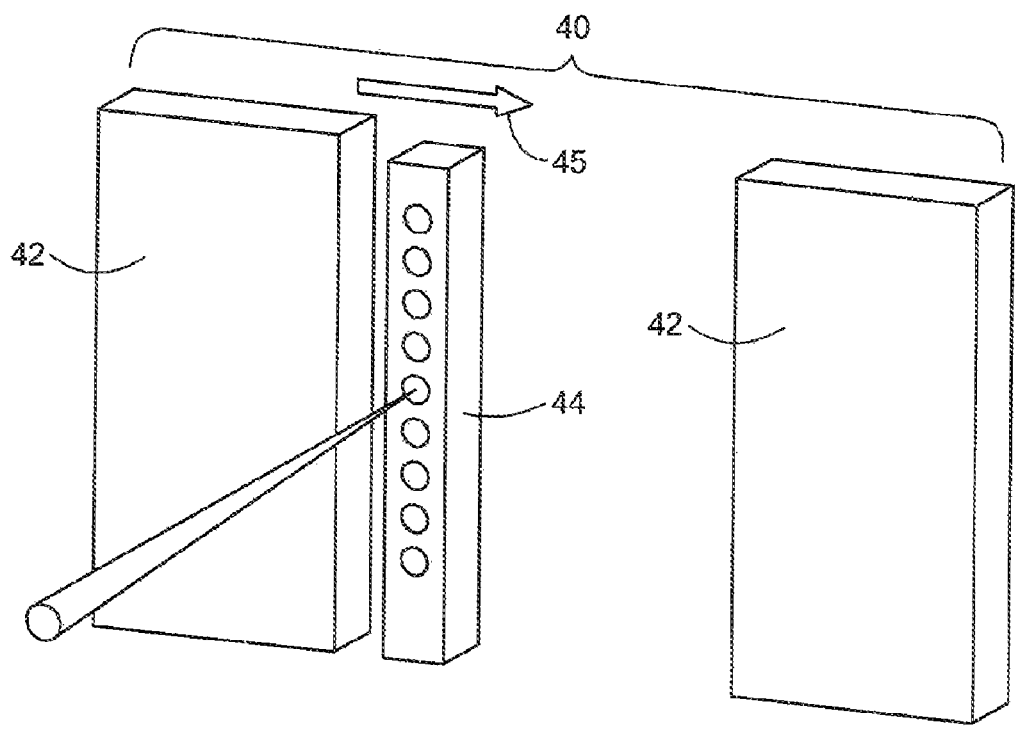
FIG. 4 shows the use of a single-dimensional array of discrete sources and a fixed set of backscatter detectors in a backscatter imaging application, in accordance with a preferred embodiment of the present invention.

A translated array in accordance with embodiments depicted in FIGS. 2 and 4 constructs an image in one pass, line by line, delivering the same X-ray dose per unit area of the target, in a fixed time (depending on the translation speed). The rotating cylinder 54 of FIG. 5 can create a low statistics image for each pass of a one-dimensional array, adding it to the global image. This concept may be referred to as a "continuously-accumulated image" (CAI). The CAI concept is useful when a limited dose to target is required or the flux per pass in insufficient. A operator stops the scan when the details in the target image are satisfactory. One application in which CAI is useful is in imaging a piece of luggage suspected to contain an improvised explosive device (IED) with an X-ray activated trigger. In this mode of operation, the initial current per pixel is low. The image is formed in multiple passes, to avoid a trigger, but enough to see meaningful details inside.

At the expense of the scan time, the cylindrical system can compensate for lost sources in one array, if a simple raster scan is used.

Finally, discrete X-ray sources, as described in the foregoing, may advantageously be employed for X-ray fluorescence mapping or spectral imaging to create an almost instantaneous material identification of a surface. Such applications requires detectors with proper energy resolution to identify the fluorescence lines.

In accordance with further embodiments of the present invention, carbon nanotube x-ray sources configured in a linear or two-dimensional array are triggered sequentially as described above. Other discrete x-ray sources that currently exist or that may be developed in the future may also be employed in a substantially similar manner, and are within the scope of the present invention as described herein and as claimed in any appended claims.

The use of x-ray source arrays of this type for this application may be particularly advantageous for the following reasons:

The x-ray source can be very compact, especially in the dimension along the line of x-ray emission.

Use of a linear array of x-ray beams advantageously reduces image distortion associated with single point sources.

This approach to generating x-rays provides flexibility in image acquisition, geometry and footprint that is far superior to current single point x-ray source-based systems.

By using sequential triggering of the linear array of x-ray sources, a backscatter image can be acquired without cross-talk between sources.

This invention, when applied in a configuration that simultaneously captures two or more views of the person being scanned, advantageously enhances the throughput of inspected subjects.

Another embodiment of the invention is now described with reference to FIG. 6A. Sets of carbon nanotube x-ray sources 110 configured as linear arrays 111, or as a two-dimensional array, are placed above (as shown) or at the sides of, a person 112 being scanned. It is to be understood that a person is shown as a representative object of inspection, but that the apparatus and methods taught herein are of valuable applicability to any object, whether animate or inanimate.

Scatter detectors 114, which may be backscatter or sidescatter detectors, for example, are positioned to capture scattered x-rays. The person being scanned walks through the x-ray beams 116 or is transported through by means such as a conveyor 118 or people mover. A hand-hold 119 may also be provided. Separate sources 110 may be activated sequentially to provide spatial resolution in accordance with known algorithms.

Figure 6A:
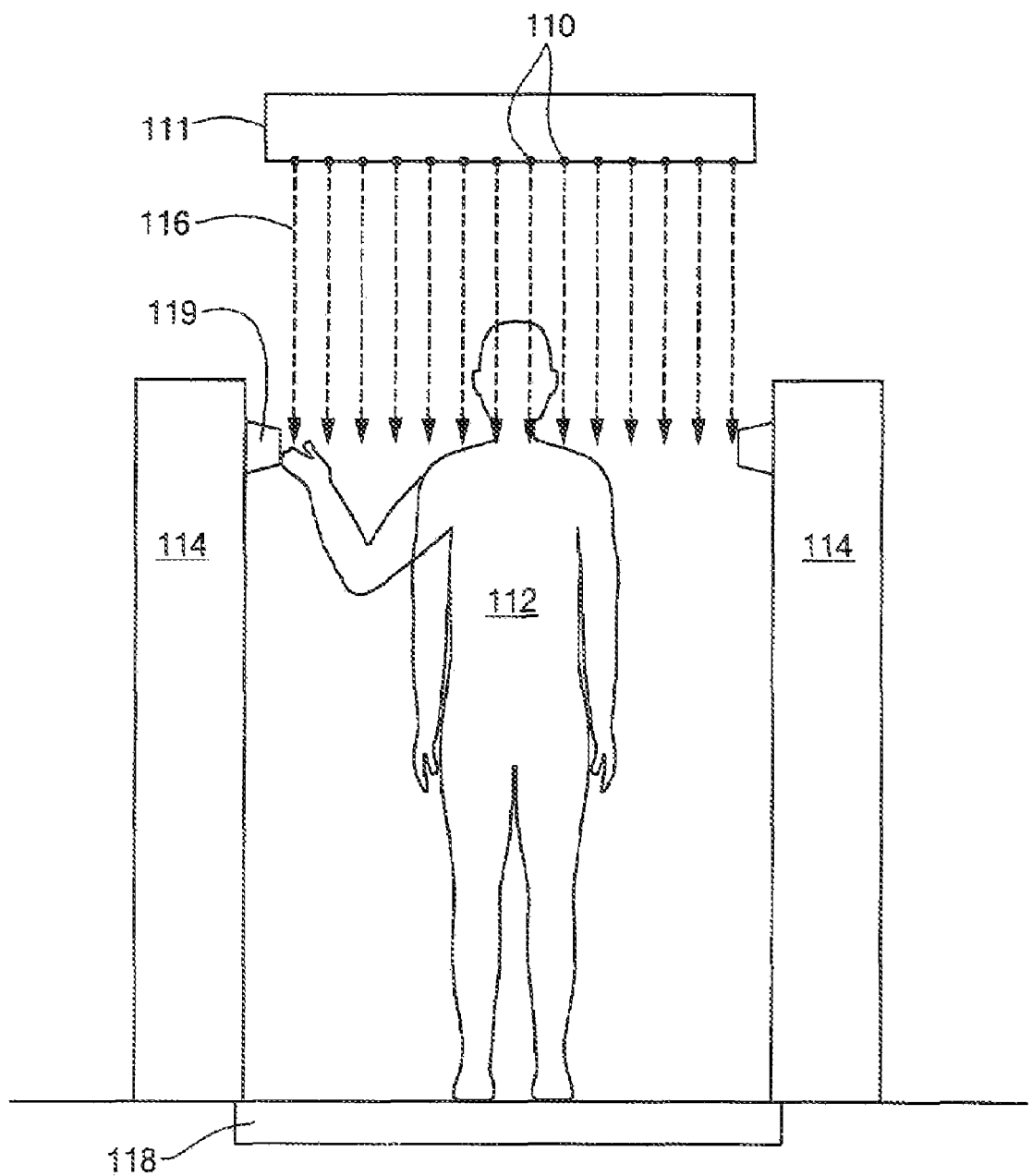
FIG. 6A shows a front view of an embodiment of the present invention in which x-rays are emitted from above.

FIG. 6B depicts subject 12 in successive positions traversing a inspection station that is designated generally by numeral 100. Inspection station 100 has a front source 160 and a back source 162, each of which may contain linear arrays, such as source 111 depicted in FIG. 6A, each of which is comprised of multiple discrete x-ray sources disposed along an axis transverse to the page. Subject 112 either walks, or is conveyed by conveyor 118, in such a manner as to have different parts of his/her person scanned by respective sources 160 and 162 during the course of traversing the inspection station.

Figure 7A:
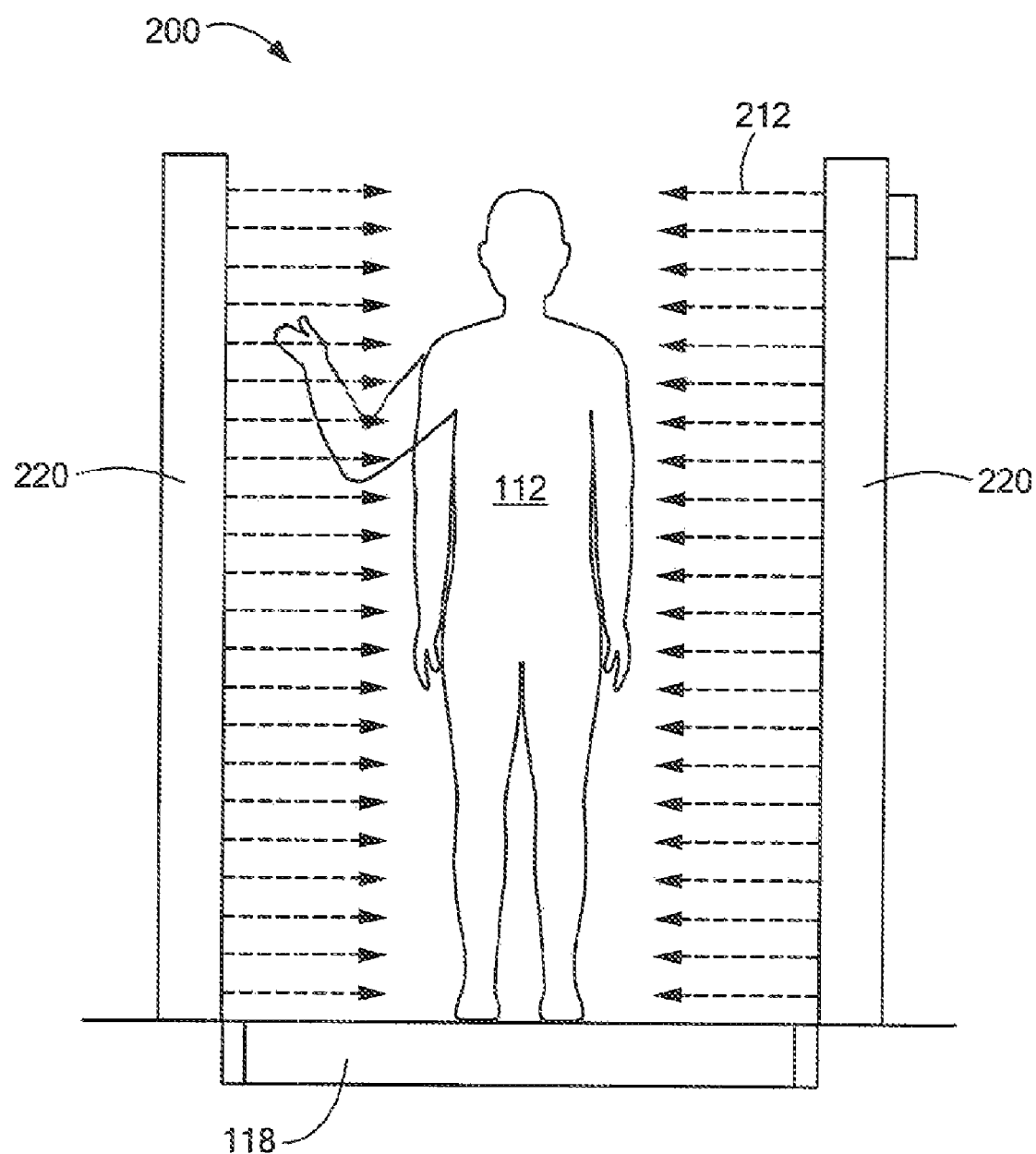
FIG. 7A shows a front view of an embodiment of the present invention in which x-rays are emitted from opposing sides.
Figure 7B:
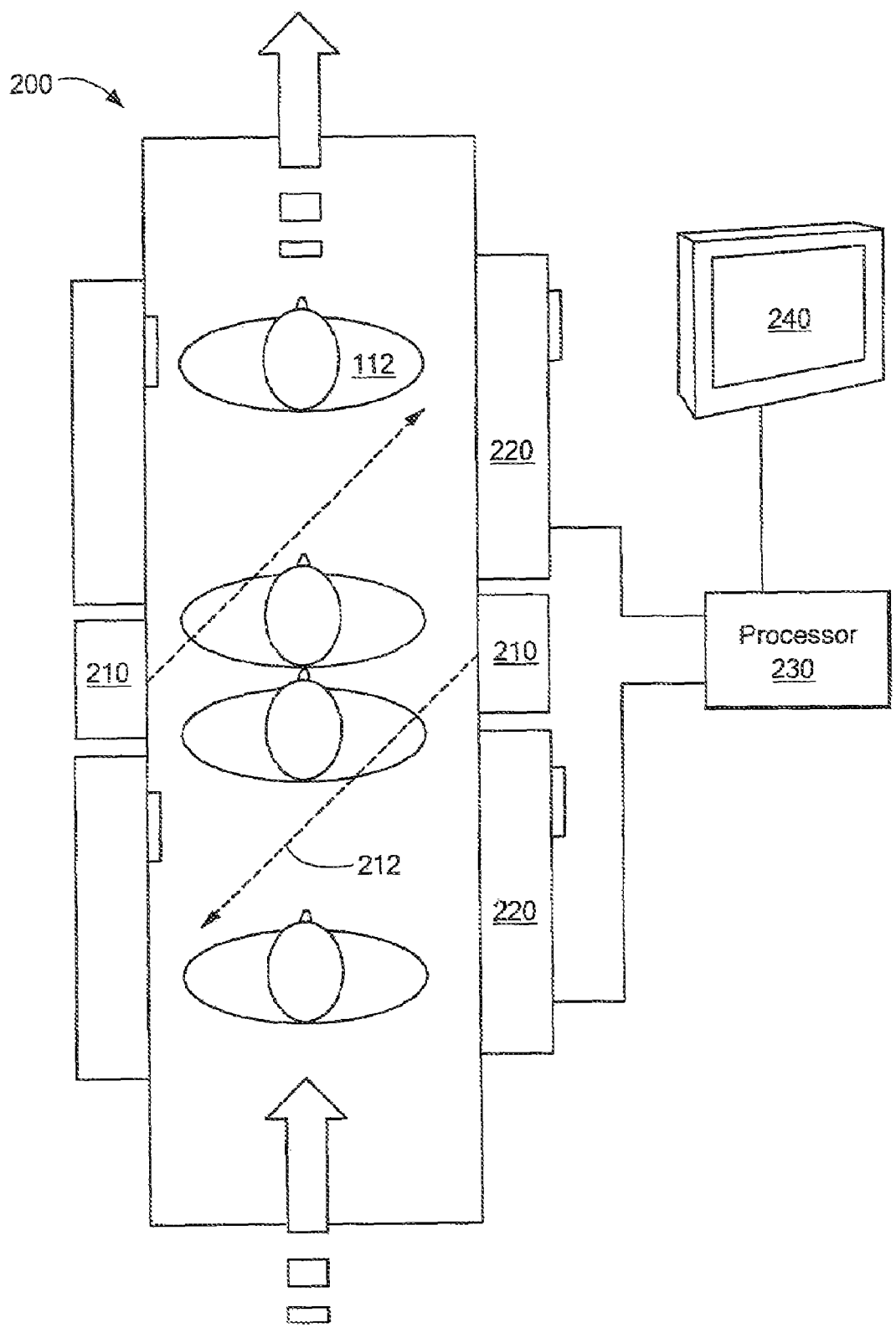
FIG. 7B shows a schematic side view of an embodiment of the present invention, depicting a person at successive positions traversing a plurality of x-ray beams emitted from above.

Yet a further embodiment of the present invention is shown in FIGS. 7A and 7B, in a configuration approaching that of metal detectors in current use. As shown in the top view of FIG. 7B, x-ray source arrays 210 emit x-rays 212, viewed most clearly in the front view of FIG. 2A. X-rays 212 impinge upon subject 112 as he/she traverses the inspection station, designated generally by numeral 200. Radiation scattered by subject 112 or by objects carried or worn on the subject's person is detected by scatter detectors 220. Scatter detectors 220 generate scatter signals on the basis of the penetrating radiation they detect, and the scatter signals are processed by processor 230 to detect and identify threat materials and objects in accordance with known algorithms, or, otherwise, to display a suitably processed image of the inspected subject at display monitor 240. In either case, an image is generated, with the term "image," as used herein and in any appended claims, signifying an ordered array of values corresponding to spatially distinct elements of the inspected object. Since the geometry minimizes distortion and shadowing of the image data, automated detection techniques that rely on shape recognition greatly benefit from the reduced image distortion and shadowing. These advantages may also be applied to conventional transmission and backscatter baggage systems.

All of the heretofore described embodiments of the invention are intended to be merely exemplary and numerous variations and modifications will be apparent to those skilled in the art. All such variations and modifications are intended to be within the scope of the present invention as defined in any appended claims.

What is claimed is:

1. A method for imaging an object, the method comprising:
   a. activating an array of discrete X-ray sources in a prescribed temporal pattern so as to illuminate the object with a beam varying in spatial orientation;
   b. detecting with a detector X-rays of the beam scattered after interaction with the object and generating a detector signal; and
   c. constructing an image of the object based on the time variation of the detector signal.

2. A method in accordance with claim 1, wherein the step of activating further includes moving the array of discrete X-ray sources with respect to the detector.

3. A method in accordance with claim 1, wherein the step of activating further includes rotating the array of discrete X-ray sources with respect to the detector about an axis.

4. A method in accordance with claim 1, wherein the step of activating further includes translating the array of discrete X-ray sources with respect to the detector.

5. A method in accordance with claim 4, wherein the array of discrete X-ray sources is characterized by an array axis, and wherein the step of activating includes translating the array in a direction substantially transverse to the array axis.

6. A method in accordance with claim 1, wherein the prescribed temporal pattern constitutes a Hadamard code.

7. A method in accordance with claim 1, wherein the step of activating discrete X-ray sources includes activating field emission sources.

8. A method in accordance with claim 7, wherein the step of activating discrete X-ray sources includes activating a plurality of field emission sources, each field emission source including a reflective target.

9. A method in accordance with claim 7, wherein the step of activating discrete X-ray sources includes activating a plurality of field emission sources, each field emission source including a transmission target.

10. An inspection system for inspecting an object, the inspection system comprising:
    a. a plurality of linear arrays of discrete sources of penetrating radiation;
    b. at least one scatter detector configured to generate a scatter signal based upon detection of penetrating radiation scattered by the inspected object; and
    c. a processor for receiving the scatter signal and generating an image of the object.

11. An inspection system in accordance with claim 10, wherein the discrete sources of penetrating radiation are carbon nanotube x-ray sources.

12. A method for inspecting an object, the method comprising:
    a. illuminating the object with a plurality of linear arrays of discrete sources of penetrating radiation;
    b. generating a scatter signal based upon detection of penetrating radiation scattered by the inspected object; and
    c. processing the scatter signal to generate an image of the object.

13. A method in accordance with claim 12, further comprising moving the object during a course of illumination by the plurality of linear arrays.

* * * * *